United States Patent
Dagel et al.

(10) Patent No.: US 6,766,865 B1
(45) Date of Patent: Jul. 27, 2004

(54) ROTARY SOIL PROBE

(76) Inventors: John H. Dagel, 110 9th St. West, Sibley, IA (US) 51249; Matt B. Hesse, 414 8th St., Sibley, IA (US) 51249; Roger J. Ackerman, 405 Oak Dr., Sibley, IA (US) 51249

( * ) Notice: Subject to any disclaimer, the term of this patent is extended or adjusted under 35 U.S.C. 154(b) by 43 days.

(21) Appl. No.: 10/086,360

(22) Filed: Mar. 1, 2002

(51) Int. Cl.⁷ .................................................. A01B 45/02
(52) U.S. Cl. ...................... 172/22; 172/547; 172/540; 172/457; 172/246; 172/254
(58) Field of Search .......................... 172/246, 254, 172/1, 22, 21, 547, 539, 540, 544, 452, 457

(56) References Cited

U.S. PATENT DOCUMENTS

| | | | |
|---|---|---|---|
| 2,543,888 A | | 3/1951 | Bunch |
| 3,331,249 A | | 7/1967 | Boxrud |
| 3,646,504 A | | 2/1972 | Stange |
| RE30,705 E | * | 8/1981 | Hines ........................... 172/22 |
| RE30,901 E | | 4/1982 | Boxrud |
| 4,326,591 A | | 4/1982 | Dedoes |
| 4,516,638 A | * | 5/1985 | Hicks et al. ................... 172/22 |
| 4,723,607 A | * | 2/1988 | Hansen ......................... 172/22 |
| 4,828,047 A | | 5/1989 | Rogerson |
| 4,869,115 A | | 9/1989 | Edwards et al. |
| D305,337 S | | 1/1990 | Plummer |
| 5,741,983 A | * | 4/1998 | Skotnikov et al. ......... 73/864.45 |
| 6,253,858 B1 | * | 7/2001 | Warke .......................... 172/22 |
| 6,321,849 B1 | * | 11/2001 | Underhill ...................... 172/22 |

FOREIGN PATENT DOCUMENTS

WO    WO 98/53312    11/1998

* cited by examiner

*Primary Examiner*—Victor Baton
(74) *Attorney, Agent, or Firm*—Mckee, Voorhees & Sease, P.L.C.

(57) ABSTRACT

An improved rotary soil probe is provided with a frame pivotally mounted on the rear of a truck or vehicle for movement about a horizontal axis between raised and lowered positions. A rotatable wheel is pivotally mounted to the frame for movement about an upwardly angled axis between an extended use position and a folded transport position. The wheel includes probes extending radially outwardly from the perimeter of the wheel. The probes are adapted to receive soil samples as the wheel is rolled along the ground. Plunger assemblies automatically discharge the soil samples on each rotation of the wheel so that the samples can be continuously collected, without the need to stop to clean out the soil samples.

12 Claims, 5 Drawing Sheets

Fig. 5

ROTARY SOIL PROBE

BACKGROUND OF THE INVENTION

Soil probes are well known in the art for collecting soil samples. These prior art soil samplers take a variety of forms, including a rotary wheel with a soil probe extending radially outwardly from the perimeter of the wheel. Such rotary probes are typically pulled behind a vehicle such that the probe penetrates the soil near the six o'clock position and then is withdrawn from the soil as the rotation of the wheel continues. Thus, the soil sample is received in the open outer end of the probe. The soil sample then is discharged through the inner end of the probe and deposited in a container positioned within the perimeter of the wheel.

Such prior art rotary soil probes have several shortcomings. For example, the soil samples occasionally become compacted in the probes and do not discharge through the inner end into the compartment. Also, the samples cannot be easily removed from the compartment without stopping the wheel. Also, the wheel is relatively large in diameter such that its size presents a hazard when transporting the wheel down a roadway, since the wheel extends substantially behind the rear of the vehicle upon which it is mounted.

Also, conventional rotary soil probes are relatively slow. For example, one known rotary probe covers approximately 80 acres per hour.

Therefore, a primary objective of the present invention is the provision of an improved rotary soil probe.

Another objective of the present invention is the provision of a rotary soil probe wheel having a plurality of probes with open outer ends through which the soil sample is collected and discharged.

A further objective of the present invention is the provision of an improved rotary soil probe which can be raised and lowered between operative and inoperative positions, and which can be folded between a use and transport position.

Another objective of the present invention is the provision of a rotary soil probe having plunger assemblies for discharging the soil samples from the probes.

A further objective of the present invention is the provision of an improved rotary soil probe which is fast and easy to use, and which may cover several hundred acres per hour.

Still another objective of the present invention is the provision of a rotary soil probe which is economical to manufacture and durable in use.

These and other objectives will become apparent from the following description of the invention.

BRIEF SUMMARY OF THE INVENTION

The soil probe of the present invention includes a frame mounted to the rear of a vehicle, such as a pickup truck. The frame has a first section which is pivotal about a horizontal axis, and a second section which is pivotal about a vertical axis. A wheel is rotatably mounted on the second frame section and has a perimeter with a plurality of soil probes extending radially outwardly therefrom. The pivotal connections of the frame sections allows the wheel to be raised and lowered and to be folded between a longitudinally extended use position and a laterally extending transport position. A plunger assembly is associated with each probe, with each assembly including an arm pivotally mounted on the wheel and a rod pivotally mounted on the arm. A cam surface engages the arm as the wheel turns to move the rod from an retracted to an extended position with respect to the probe. As the rod is extended into the probe, the soil sample received in the outer end of the probe is discharged through the outer end for collection. Thus, the rotary soil probe of the present invention can be operated continuously without stopping to collect the soil samples.

DETAILED DESCRIPTION OF THE INVENTION

The rotary soil probe of the present invention is generally designated by the reference numeral 10 in the drawings. The probe 10 includes a frame 12 adapted to be mounted on the back of a vehicle, such as a pickup truck 14, and a wheel 16 rotatably mounted on the frame 12. The wheel 16 includes a plurality of probes 18 adapted to pull soil samples from the soil as the truck moves forwardly to rotate the wheel over the soil. The probes each have a beveled outer end and at least one axially extending slot 19 to facilitate collection and discharge of soil to and from the probe 18.

More particularly, the frame 12 of the soil probe 10 includes a first section 20 mounted to the truck for pivotal movement about a horizontal axis, and a second section 22 pivotally connected to the first section 20 for movement about a substantially vertical axis. The first frame section 20 includes an elongated member preferably mounted on the rear bumper of the truck 14 so as to be horizontally disposed, with the longitudinal axis of the member 20 defining the horizontal pivot axis for the first frame section 20. A leg 20 extends downwardly from the member 24 and is connected to the extensible rod 28 of a hydraulic cylinder 30. The cylinder 30 is mounted to the frame of the truck 14 and is operatively connected to a hydraulic fluid source (not shown). The controls for the hydraulic cylinder 30 are preferably located in the bed of the truck 14 so that an assistant riding in the back of the truck can operate the cylinder 30.

Figure 1:
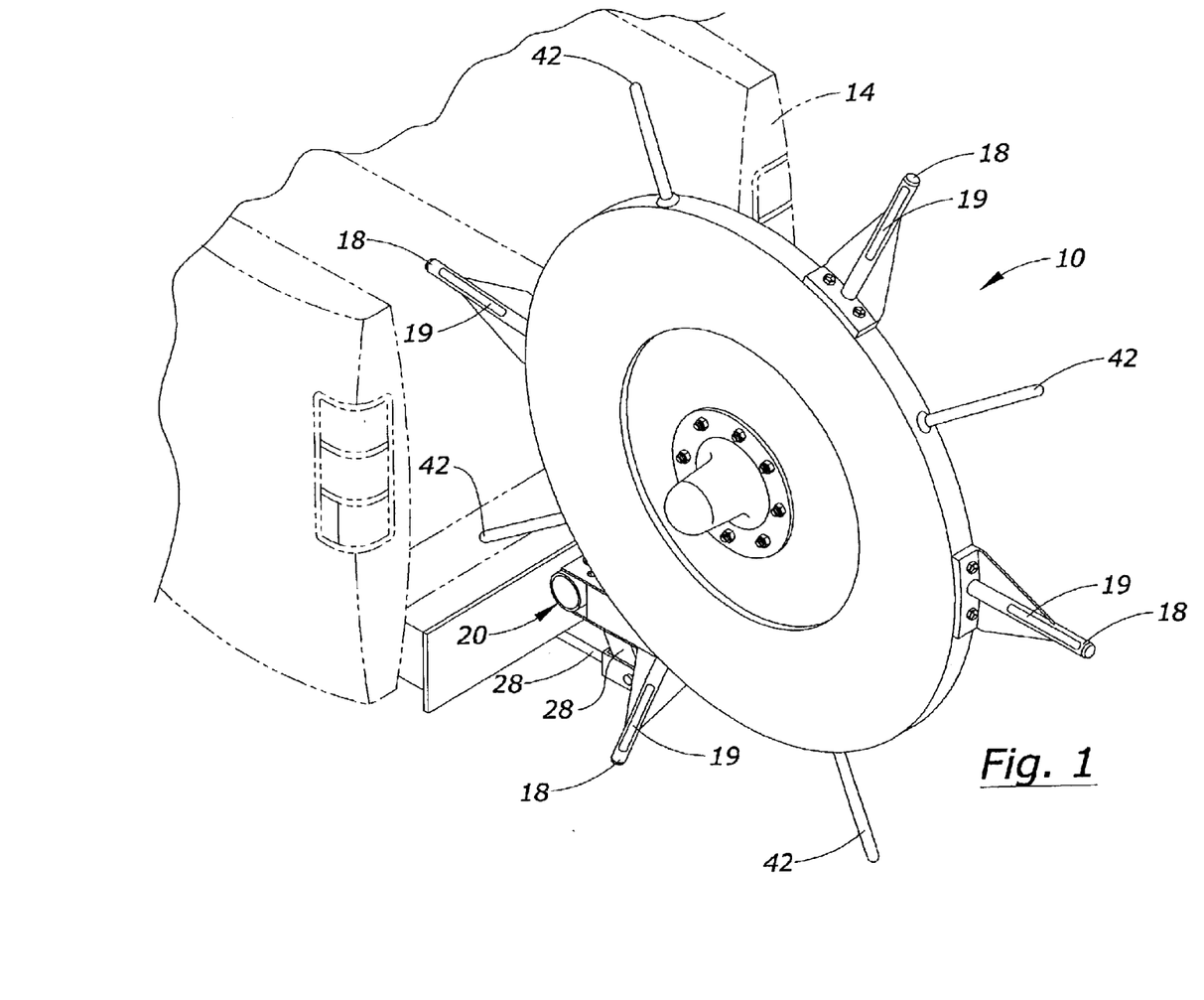
FIG. 1 is a rear perspective view of the rotary soil probe of the present invention mounted on the back of a pickup truck.
Figure 2:
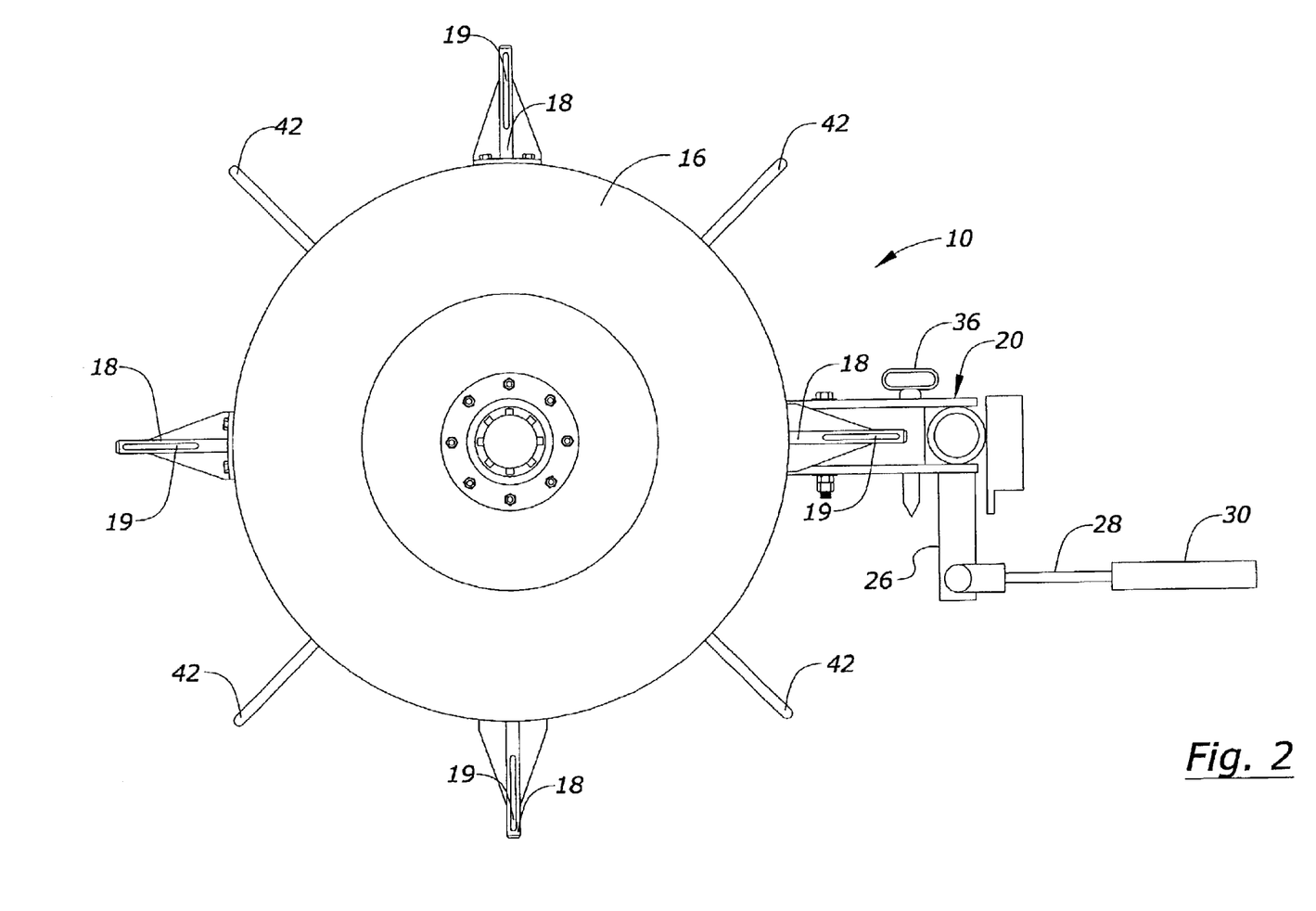
FIG. 2 is a side elevation view from one side of the soil probe.

A yoke 32, defined by a pair of spaced apart arms, extends rearwardly from the elongated member 24. The inner end of the second frame section 22 extends between the plates of the yoke 32 and is pivotally connected thereto by a bolt 34. The bolt 34 defines a substantially vertical or upwardly angled pivot axis about which the second frame section 22 pivots relative to the first frame section 20, such that the second frame section 22 is moveable between a rearwardly extending use position, shown in FIGS. 1–3, and a laterally extending folded or transport position, shown in FIG. 4. The inner terminal end of the second frame section 22 includes a hole adapted to receive a lock pin 36 extending through aligned slots 38 in the plates of the yoke 32. The pin 36 retains the second frame section 22 and the attached wheel 16 in the extended use position, while the slots 38 allow an angle of play, preferably 10°–15°, in the alignment of the first frame section 20 and the yoke 32, so as to prevent binding of the wheel 16 if the truck 14 deviates slightly from a straight line path. In the folded transport position, the weight of the wheel 16 and the angled axis of bolt 34 keeps the soil probe 10 in the transport position.

The outer end of the second frame section 22 includes a hub 40 upon which the wheel 16 is rotatably mounted. The four probes 18 extend radially from the outer perimeter of the wheel 16 and are spaced equally around the wheel at 90° intervals. A plurality of spikes 42 extend radially outwardly from the perimeter of the wheel 16, and are spaced at 90° intervals around the wheel between the probes 18. When the wheel 16 is in a ground engaging use position, the probes 16 and spikes 42 penetrate the ground and cause the wheel 16 to rotate as the truck 14 moves forwardly. The probes 18 are hollow tubes, and preferably include a longitudinally extending slot 44, which facilitates receipt and discharge of soil samples from the probes 18.

Figure 3:
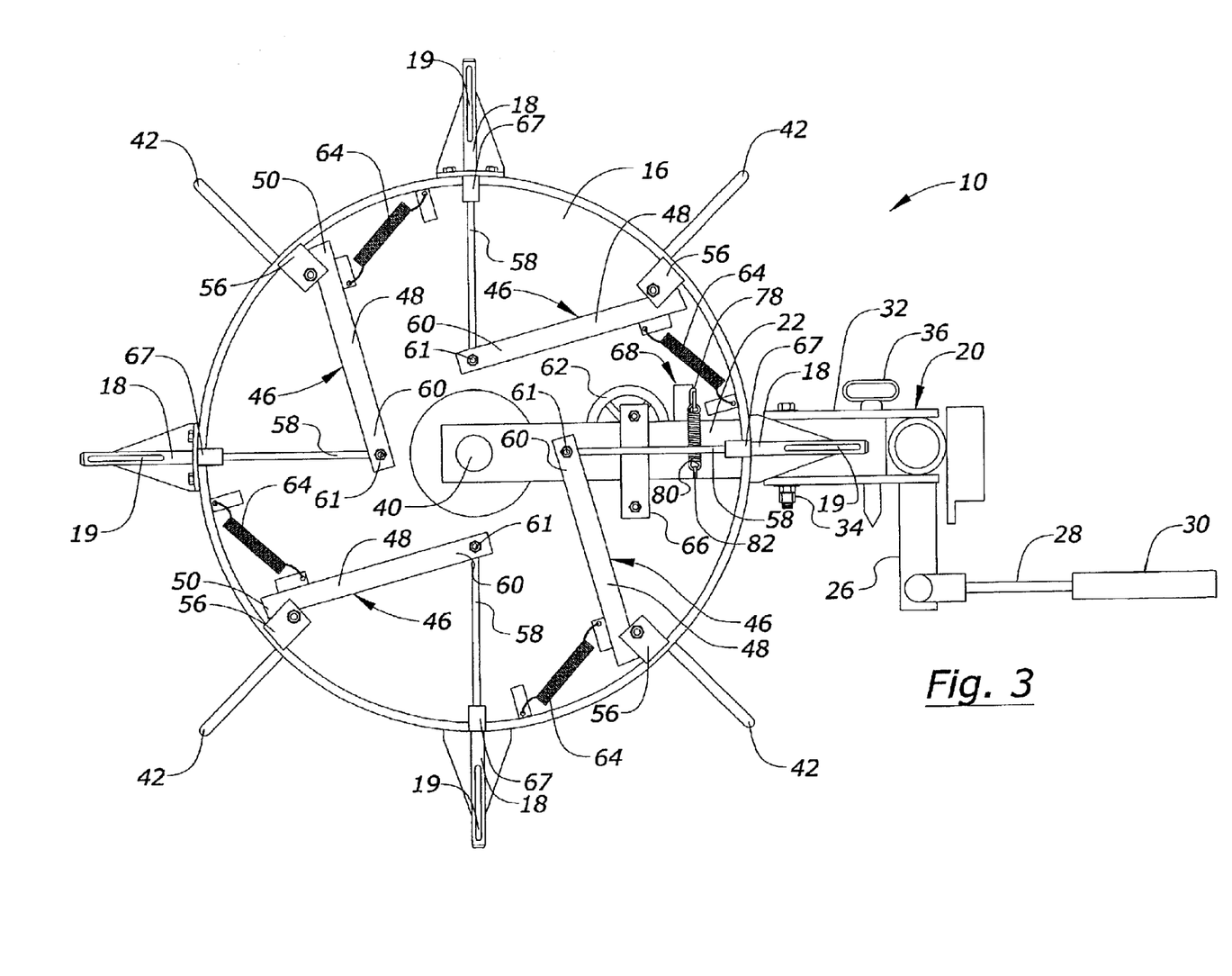
FIG. 3 is a side elevation view from the opposite side of the soil probe.

A plurality of plunger assemblies 46 are pivotally mounted on the inner face of the wheel 16, as best seen in FIG. 3. Each of the plunger assemblies 46 is associated with one of the probes 16. Each plunger assembly 46 includes an arm 48 having a first end 50 having a tubular collar 52 welded thereto in a transverse relationship to the longitudinal axis of the arm 48. A bolt 54 extends through the wheel 16, the collar 52, and a tab 56 extending inwardly from the perimeter of the wheel 16. The bolt 54 defines a pivot axis for the outer end 50 of the arm 48.

Figure 5:
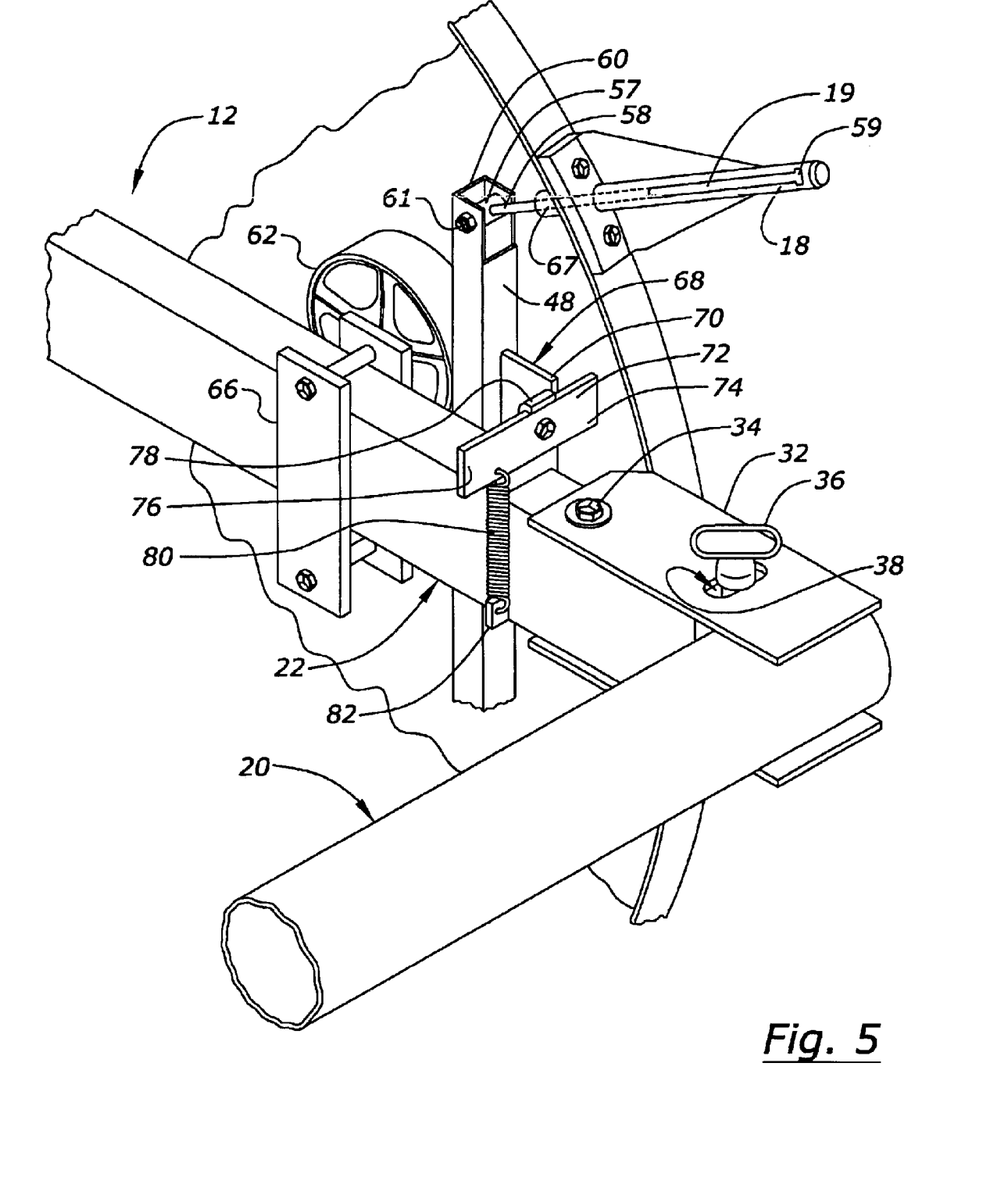
FIG. 5 is a perspective view showing the inside of the wheel, the plunger assembly and an anti-reverse mechanism.

Each plunger assembly also includes a rod 58. The inner end of the rod 58 is pivotally connected to the inner end 60 of the arm 48. The inner end of the rod 58 is connected to a transverse collar 57 received within a cut out in the square tubular arm 48 and is pivotally secured in place with a nut and bolt assembly 61, as best seen in FIG. 5. The outer end of the rod 58 has an enlarged head 59 and is adapted to slide within the hollow probe 18 so as to discharge the soil sample collected by the probe 18 during each rotation of the wheel 16. The extension of the rod 58 into the probe 18 is accomplished by a cam wheel 62 which engages the arm 48 after the probe 18 is withdrawn from the soil. As best seen in FIG. 3, the cam wheel 62 engages the arm 48 at approximately a two o'clock position. As the clockwise rotation of the wheel 16 continues, the cam wheel 62 causes the arm 48 to pivot in a clockwise direction (as seen in FIG. 3) about the horizontal axis defined by the bolt 54, thereby extending the rod 58 into the probe 18 such that the head 59 pushes out the soil sample contained in the probe 18. After the inner end 60 of the arm 48 moves past the cam wheel 62, the rod 58 is automatically urged to the retracted position by a spring 64 connected between the wheel 16 and the arm 48. The cam wheel 62 is adjustably mounted on the second frame section 22 with a mounting bracket 66. The guide collar 67 is axially aligned with the probe 18 to guide the extension and retraction of the rod 58 relative to the probe 18.

The second frame section 62 also includes an anti-reverse mechanism 68 to prevent the wheel from rotating counterclockwise. More particularly, the anti-reverse mechanism 68 includes a bar 70 mounted on the second frame section 22 and extending upwardly therefrom. An arm 72 is pivotally mounted to the bar 70 and extends laterally or transversely. The arm 72 has one end 74 extending toward the wheel 16 a sufficient distance to engage the tab 56 on the wheel 16. The opposite end 76 of the arm 72 extends away from the wheel 16. The bar 70 includes a stop element 78 which prevents the arm 72 from rotating clockwise, as seen in FIG. 5, beyond the transverse position. Upon the normal clockwise rotation of the wheel 16, the bottom edge of the tab 56 engages the arm 72 and rotates it downwardly against the bias of the spring 80. After the tab 56 passes beyond the arm 72, the spring 80 urges the arm 72 back to the transverse position shown in FIG. 5. If the wheel starts to rotate counterclockwise, which may occur when it is raised from the ground engaging position. The arm 72 will engage the top edge of the tab 56 to prevent further counterclockwise rotation of the wheel. Otherwise, the retracted rod 58 below the cam wheel 62 would hit the cam wheel and be bent or damaged.

Figure 4:
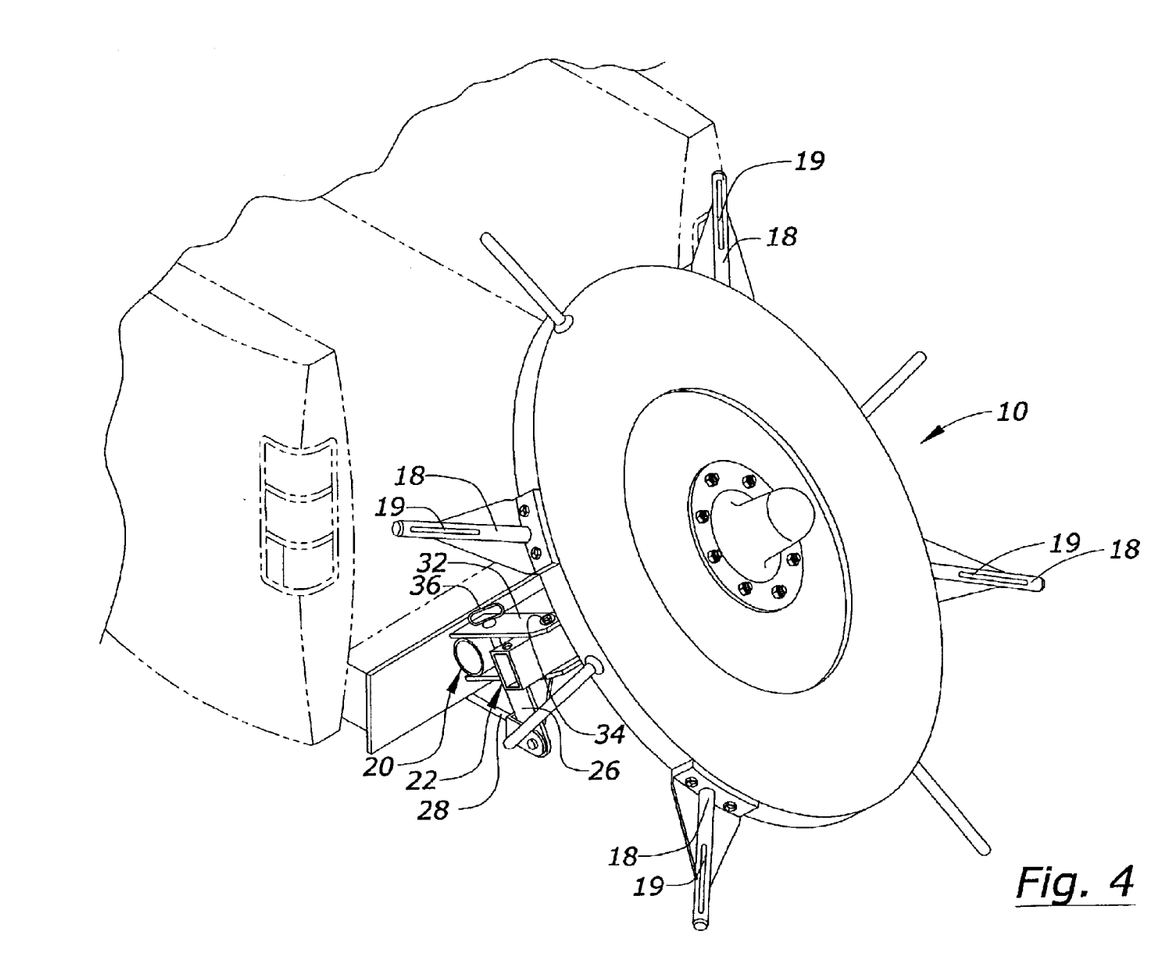
FIG. 4 is a perspective view showing the soil probe folded to the transport position.

The soil probe 10 is transported to the field or soil sampling site by the truck 14 with the wheel 16 folded to the transport position, as seen in FIG. 4. In the transport go position, the wheel has been raised, by the extension of the hydraulic cylinder rod 28, such that the probes 18 do not engage the ground. The wheel 16 remains in the transport position due to the inclined orientation of the pivot axis defined by the bolt 34 and the weight of the wheel 16.

Upon arrival at the desired location, the lock pin 36 is removed from the yoke 32 and the wheel 16 is manually folded from the transport position to the use position. The hydraulic cylinder 30 is then actuated so as to retract the rod 28, thereby lowering the wheel so that the probes 18 and spikes 42 will be forced into the ground. The lock pin 36 is reinserted into the yoke 32 and through the aligned hole in the second frame section 22 to limit the lateral movement of the wheel 16 to a relatively small angular range, preferably between 10°–15°.

The truck can then be driven forwardly such that the wheel 16 rolls upon the ground, with each probe 18 collecting a soil sample as it is inserted into and withdrawn from the ground. As the rotation of the wheel 16 continues, the cam wheel 62 engages the lever arm 48 to extend the plunger rod 58 into the associated probe 18 to expel the soil sample from the outer end of the probe 18. Preferably, the probes 18 include a longitudinal slot which facilitates collection and discharge of the soil sample from the probe 18. An assistant riding in the back of the truck 14 collects the soil samples in any desired container as the sample is expelled from the probe 18 by the extended plunger rod 58. As the lever arm passes beyond the cam wheel 62, the spring 64 retracts the rod 58 so that the probe is ready to collect another soil sample.

Whereas the invention has been shown and described in connection with the preferred embodiment thereof, it will be understood that any modifications, substitutions, and additions may be made which are within the intended broad scope of the following claims. From the foregoing, it can be seen that the present invention accomplishes at least all of the stated objectives.

What is claimed is:

1. A soil probe for collecting soil samples, comprising:
   a frame adapted to be pivotally mounted to a vehicle and having first and second sections;
   a wheel rotatably mounted on the second section of the frame, and having a perimeter with a plurality of soil probes extending radially outward from the perimeter for collecting soil samples;
   a hydraulic cylinder extending between the vehicle and the first section of the frame for moving the wheel between raised and lowered positions;
   the first and second sections of the frame being pivotally connected such that the wheel is movable between a longitudinally extended use position and a laterally folded transport position;
   each probe having an outer end for receiving and discharging the soil sample;

wherein the wheel includes a plurality of plunger assemblies, each plunger assembly being associated with one of the probes and being movable between an inoperative retracted position and an extended position within the probe to expel a soil sample from the probe; and wherein the plunger assemblies are biased toward the retracted position.

2. A soil probe for collecting soil samples, comprising:

a frame adapted to be pivotally mounted to a vehicle and having first and second sections;

a wheel rotatably mounted on the second section of the frame, and having a perimeter with a plurality of soil probes extending radially outward from the perimeter for collecting soil samples;

a hydraulic cylinder extending between the vehicle and the first section of the frame for moving the wheel between raised and lowered positions;

the first and second sections of the frame being pivotally connected such that the wheel is movable between a longitudinally extended use position and a laterally folded transport position;

each probe having an outer end for receiving and discharging the soil sample;

wherein the wheel includes a plurality of plunger assemblies, each plunger assembly being associated with one of the probes and being movable between an inoperative retracted position and an extended position within the probe to expel a soil sample from the probe; and where the plunger assemblies are pivotally mounted on the wheel for movement between the retracted and extended positions.

3. A soil probe for collecting soil samples, comprising:

a frame adapted to be pivotally mounted to a vehicle and having first and second sections;

a wheel rotatably mounted on the second section of the frame, and having a perimeter with a purality of soil probes extending radially outward from the perimeter for collecting soil samples;

a hydraulic cylinder extending between the vehicle and the first section of the frame for moving the wheel between raised and lowered positions;

the first and second sections of the frame being pivotally connected such that the wheel is movable between a longitudinally extended use position and a laterally folded transport position;

each probe having an outer end for receiving and discharging the soil sample; wherein the wheel includes a plurality of plunger assemblies, each plunger assembly being associated with one of the probes and being movable between an inoperative retracted position and an extended position within the probe to expel a soil sample from the probe; and wherein the wheel includes a cam and the plunger assemblies are moved from the retracted position to the extended position by the cam.

4. A soil probe for collecting soil samples, comprising:

a frame adapted to be pivotally mounted to a vehicle and having first and second sections;

a wheel rotatably mounted on the second section of the frame, and having a perimeter with a plurality of soil probes extending radially outward from the perimeter for collecting soil samples;

a hydraulic cylinder extending between the vehicle and the first section of the frame for moving the wheel between raised and lowered positions;

the first and second sections of the frame being pivotally connected such that the wheel is movable between a longitudinally extended use position and a laterally folded transport position;

each probe having an outer end for receiving and discharging the soil sample;

wherein the wheel includes a plurity of plunge assemblies, each plunger assembly being associated with one of the probes and being movable between an inoperative retracted position and an extended position within the probe to expel a soil sample from the probe; and wherein each plunger assembly includes a pivot arm and a clean out rod, the rod being aligned with the associated probe for axial movement with respect to the probe.

5. A soil probe for collecting soil samples, comprising:

a frame adapted to be pivotally mounted to a vehicle and having first and second sections;

a wheel rotatably mounted on the second section of the frame, and having a perimeter with a plurality of soil probes extending radially outward from the perimeter for collecting soil samples;

a hydraulic cylinder extending between the vehicle and the first section of the frame for moving the wheel between raised and lowered positions;

the first and second sections of the frame being pivotally connected such that the wheel is movable between a longitudinally extended use position and a laterally folded transport position;

each probe having an outer end for receiving and discharging the soil sample;

a pin removable extending through the first and second sections to retain the wheel in the use positions; and wherein one of the first and second frame sections includes a slot through which the pin extends to allow a range of angular movement between the first and second frame sections.

6. A soil probe for collecting soil samples, comprising:

a frame adapted to be pivotally mounted to a vehicle and having first and second sections;

a wheel rotatably mounted on the second section of the frame, and having a perimeter with a plurality of soil probes extending radially outward from the perimeter for collecting soil samples;

a hydraulic cylinder extending between the vehicle and the first section of the frame for moving the wheel between raised and lowered positions;

the first and second sections of the frame being pivotally connected such that the wheel is movable between a longitudinally extended use position and a laterally folded transport position;

each probe having an outer end for receiving and discharging the soil sample; and wherein a spike is positioned between adjacent probes.

7. A soil for collecting soil samples, comprising:

a frame adapted to be pivotally mounted to a vehicle and having first and second sections;

a wheel rotatably mounted on the second section of the frame, and having a perimeter with a plurality of soil probes extending radially outward from the perimeter for collecting soil samples;

a hydraulic cylinder extending between the vehicle and the first section of the frame for moving the wheel between raised and lowered positions;

the first and second sections of the frame being pivotally connected such that the wheel is movable between a longitudinally extended use position and a laterally folded transport position;

each probe having and outer end for receiving and discharging the soil sample; and an arm mounted on the frame and adapted to engage a portion of the wheel to prevent reverse rotation of the wheel.

8. A soil probe for collecting soil samples, comprising:

a frame adapted to be mounted on a vehicle;

wheel rotatably mounted on the frame;

at least one probe extending outwardly from the wheel and having an outer end adapted to receive a soil sample and an inner end;

a plunger rod mounted in the wheel for movement between a retracted position adjacent the inner end of the probe and an extended position adjacent the outer end of the probe to discharge the soil sample from the outer end of the probe;

wherein the plunger rod is mounted on an arm pivotally mounted on the wheel.

9. The soil probe of claim 8 further comprising a cam on the wheel adapted to periodically engage and pivot the arm to move the plunger rod from the retracted position to the extended position.

10. The soil probe of claim 8 wherein the plunger rod is biased toward the retracted position.

11. The soil probe of claim 8 further comprising an arm mounted on the frame and adapted to engage a portion of the wheel to prevent reverse rotation of the wheel.

12. A method for obtaining a soil sample, comprising:

rotating a wheel having a probe such that the probe penetrates the soil to collect a soil sample through an open outer end of the probe;

continuing rotation of the wheel such that the probe is withdrawn from the soil with the soil sample retained in the probe; and extending a plunger rod into an inner end of the probe so as to discharge to soil sample through the outer end of the probe;

wherein the extension of the plunger rod is automatic upon continued rotation of the wheel; and wherein the extension of the plunger rod is by cam action.

* * * * *

UNITED STATES PATENT AND TRADEMARK OFFICE
CERTIFICATE OF CORRECTION

PATENT NO.   : 6,766,865 B1
DATED        : July 27, 2004
INVENTOR(S)  : Dagel et al.

It is certified that error appears in the above-identified patent and that said Letters Patent is hereby corrected as shown below:

Column 6,
Line 10, should read:
-- wherein the wheel includes a plurality of plunger --
Line 59, should read:
-- 7. A soil probe for collecting soil samples, comprising: --

Column 7,
Line 8, should read:
-- each probe having an outer end for receiving and discharging the soil sample; and --
Line 15, should read:
-- a wheel rotatably mounted on the frame; --

Column 8,
Line 18, should read:
-- as to discharge the soil sample through the outer end of the probe; --

Signed and Sealed this

Seventh Day of December, 2004

JON W. DUDAS
*Director of the United States Patent and Trademark Office*